US007055366B2

(12) United States Patent
Lewis

(10) Patent No.: US 7,055,366 B2
(45) Date of Patent: Jun. 6, 2006

(54) FLOW SENSOR CALIBRATION METHODS AND APPARATUS

(75) Inventor: Darren Lewis, Anacortes, WA (US)

(73) Assignee: Upchurch Scientific, Inc., Oak Harbor, WA (US)

( * ) Notice: Subject to any disclaimer, the term of this patent is extended or adjusted under 35 U.S.C. 154(b) by 0 days.

(21) Appl. No.: 10/851,728

(22) Filed: May 21, 2004

(65) Prior Publication Data

US 2005/0257595 A1 Nov. 24, 2005

(51) Int. Cl.
*G01F 25/00* (2006.01)
(52) U.S. Cl. ...................................................... 73/1.16
(58) Field of Classification Search .................. 73/1.16, 73/204.14, 1.34, 227; 702/100
See application file for complete search history.

(56) References Cited

U.S. PATENT DOCUMENTS

| | | | | | |
|---|---|---|---|---|---|
| 4,136,563 | A | * | 1/1979 | Mueller et al. | 73/861.03 |
| 4,335,605 | A | * | 6/1982 | Boyd | 73/204.14 |
| 5,218,866 | A | * | 6/1993 | Phillips et al. | 73/204.15 |
| 5,419,190 | A | * | 5/1995 | Boyd | 73/204.25 |
| 5,576,487 | A | * | 11/1996 | Gimson | 73/204.11 |
| 5,837,903 | A | * | 11/1998 | Weigand | 73/861.42 |
| 6,352,001 | B1 | * | 3/2002 | Wickert et al. | 73/861.52 |
| 6,378,354 | B1 | * | 4/2002 | Sharp | 73/1.16 |
| 6,404,344 | B1 | * | 6/2002 | Young | 340/606 |
| 6,616,823 | B1 | * | 9/2003 | Kopf-Sill | 204/602 |
| 2004/0055374 | A1 | * | 3/2004 | Cohen et al. | 73/204.11 |
| 2004/0118403 | A1 | * | 6/2004 | O'Connor et al. | 128/204.23 |
| 2004/0144169 | A1 | * | 7/2004 | Popielas et al. | 73/200 |

FOREIGN PATENT DOCUMENTS

GB 2195448 A * 4/1988

OTHER PUBLICATIONS

Teledyne Hastings Instruments Application Notes: Improving Accuracy in Analog Mass Flow Measurements 5th. Order Polynomical Curve Fitting, Internet Publication.*

* cited by examiner

*Primary Examiner*—Hezron Williams
*Assistant Examiner*—John Fitzgerald
(74) *Attorney, Agent, or Firm*—Vinson & Elkins L.L.P.

(57) ABSTRACT

Apparatus and methods of calibrating a microfluidic flow sensor, in which the flow of a fluid through a flow sensor is stopped and a first value is read from the flow sensor, then the fluid is pumped through the flow sensor sequentially at first and second selected rates, and readings from the flow sensor of the flow rate are taken for each of the rates. The readings are used in a polynomial equation to determine the actual flow rate, which is used to calibrate the sensor. The flow sensor can be connected to a computer programmed to perform the calibration method, determine the actual flow rate of the sensor, and make appropriate adjustments to the flow rate of a pump.

20 Claims, 24 Drawing Sheets

Nano-Flow System controller firmware V1.4 for 100ul pump
Code examples for microcontroller

Darren Lewis, Upchurch Scientific Inc., Oak Harbor, WA 98277

The Main execution loop
```
main()
{
char *a_buffer[10];
int j;
float old_rate=0,new_rate=0;
int32 k=0;
```

Setup the microcontroller
```
clear_buffer(a_buffer,10);

disable_interrupts(global);

enable_interrupts (INT_EXT);
enable_interrupts (INT_EXT1);
enable_interrupts (INT_EXT2);
enable_interrupts (INT_RDA);

setup_timer_2(T2_DISABLED,1,1);
setup_timer_1(T1_DISABLED);
setup_timer_0(RTCC_OFF);

setup_adc(ADC_CLOCK_INTERNAL);
setup_adc_ports(RA0_RA1_RA3_ANALOG);
set_adc_channel(1);

disable_interrupts (INT_RB);
disable_interrupts (INT_PSP);
disable_interrupts (INT_AD);
disable_interrupts (INT_EEPROM);
disable_interrupts (INT_TBE);
disable_interrupts (INT_CCP1);
disable_interrupts (INT_CCP2);
disable_interrupts (INT_TIMER1);

ext_int_edge( 0, H_TO_L);
ext_int_edge( 1, H_TO_L);
ext_int_edge( 2, H_TO_L);

enable_interrupts(global);
```

Setup the flow sensor
```
setup();
delay_ms(250);
```

The main event loop
```
while(1) (infinite loop)
{
delay_ms(10);
```

Figure 7A

```
    output_low(LED1);

Read current position from the motor driver
if(lynx_data_ready==TRUE)
    {
        dispatch(com_1_rec_buf,COM1);
        clear_buffer(com_1_rec_buf,25);
        lynx_data_ready=FALSE;
    }

Read the current raw flow rate from Flow Sensor
if(flow_data_ready==TRUE)
    { flow_data_ready=FALSE;
        flow_rate_sum=0;

averaging_buffer[flow_rate_index]=flow_rate;
        flow_rate_index++;
        if(flow_rate_index>time_constant)
        {
            flow_rate_index=0;
            flow_rate_buf_full=TRUE;
        } for(j=0;j<time_constant+1;j++)
        flow_rate_sum+=(int32)(averaging_buffer[j]);
        avg_flow_rate=(int16)(flow_rate_sum/(int32)(time_constant+1));//Get ave.
flow rate (raw)

Get the interpolated flow rate from the quadratic equation and the averaged raw
sensor reading (useful for display purposes because it is filtered using a
running average)

averaged_rate=(float)return_actual_rate(avg_flow_rate);//Get ave. flow
rate (fit to cal curv Get the interpolated flow rate from the quadratic equation and the instantaneous
raw sensor reading (used for feedback purposes).

new_rate=(float)return_actual_rate(flow_rate);//Get instantaneous flow
rate (fit to cal curve)

new_rate=(old_rate+new_rate)/(float)2;

old_rate=new_rate;

Perform proportional-integral-derivative (PID) on the interpolated flow sensor
reading. This function provides the negative feedback. In this instance, the
feedback is performed within the quadratic part of the sensor response (below 5
microlitres per minute). If the piston position reaches the end of stroke, the
forward velocity is set to 0. If the position is at the beginning of stroke,
the reverse velocity is set to 0.

if(!calibrating&&!do_home)//Don't do if calibrating or homing...
```

Figure 7B

```
            {
            if(!waiting)
            {
                if((speed<5000)&&(speed>=0))
                applied_speed=do_pid((float)speed,(float)new_rate);
```
…The PID compensator
```
                else
                applied_speed=speed;
```
…set applied speed to no feedback if operating above 5ul/min or below 0
```
                if((applied_speed>=0)&&(position<=100000))
                adjust_speed(applied_speed);
                else
                if((applied_speed<0)&&(position>=0))
                adjust_speed(applied_speed);//use applied speed if moving in
reverse
                else
                adjust_speed(0);
            }
            else
            adjust_speed(0);

}
        else
        adjust_speed(applied_speed);
```
…apply the no-feedback speed if calibrating or homing

```
        actual_rate=applied_speed;//added if(transmit==TRUE)
        report_values();
        delay_ms(50);
        get_position();//get the current position
        delay_ms(50);
    }
```

Figure 7C

Interpret commands from the user, if any…
```
if(host_data_ready==TRUE)
    {
        strcpy(a_buffer,"\n\r");
        if(echo)
        com_host(a_buffer);
        dispatch(host_rec_buf,HOST);
        clear_buffer(host_rec_buf,25);
        host_data_ready=FALSE;
    }
```

If the user chooses, perform calibration
```
if(calibrating&&!do_home)
do_calibration();
else
```
If the user chooses, perform homing routine
```
if(do_home&&!calibrating)
init();
```

Blink LED when homing or calibrating…

```
if(calibrating||do_home)
output_high(LED1);
else
output_low(LED2);
```

Motion commands for remote TTL operation or automatic fill/refill...

Automatic dispense
```
if(input(PIN_D7)&&!input(PIN_D6)&&!do_home&&!calibrating)
{
    speed=(float)infusion_rate;
    switch_valve(column);
    waiting=FALSE;
}
```

Automatic fill
```
if(!input(PIN_D7)&&input(PIN_D6)&&!do_home&&!calibrating)
{
    switch_valve(fill);
    speed=(float)(withdrawal_rate);
    speed=-speed;
    waiting=FALSE;
}
```

Automatic fill/dispense cycle
```
if(do_loop)
{
    if((position>(float)99990)&&!do_home&&!calibrating)
    {
        if(am_i_filling)
        {
            adjust_speed(0);
            delay_ms(50);
            adjust_speed(0);
            for(k=0;k<10;k++)
            delay_ms(1000);

switch_valve(fill);

speed=(float)(withdrawal_rate);
            speed=-speed;
            waiting=FALSE;
            am_i_filling=FALSE;
            cycle_timer=cycle_timer+2;
            write_long_vars(addr_cyc_timer,cycle_timer);

}
    } if((position<(float)10)&&!do_home&&!calibrating)
    {
        if(!am_i_filling)
        {
            adjust_speed(0);
            delay_ms(50);
            adjust_speed(0);
            for(k=0;k<10;k++)
```

Figure 7D

```
                delay_ms(1000);

switch_valve(column);
                speed=(float)(infusion_rate);
                waiting=FALSE;
                am_i_filling=TRUE;

}
        }

} the_output=(float)read_adc()/(float)204.8;

delay_ms(10);
    }
    return 1;
    }
```
…End of main function

Handle commands sent from user via RS-232…
```
void dispatch(char* command,char source)//Respond to input commands
{
signed int16 i=1;
char the_char=0;
char out_strings[25];
float new_position=0;
char err_in=FALSE;
int32 new_rate=0;//was float
char do_ok=0;

clear_buffer(out_strings,25);

if(source==HOST)
{
```
Received command to display data to user through RS-232 port…
```
    if(command[0]=='?')
        {
        if(command[1]=='0')
        {
            show_factors=0;
            show_pos=0;
            show_raw=0;
            show_calc=0;
            show_valve=0;
            show_infuse=0;
            show_withdrawal=0;
            show_output=0;
            do_ok=1;
        } if(command[1]=='1')
        {
            show_factors=1;
            show_pos=1;
            show_raw=1;
```

Figure 7E

```
            show_calc=1;
            show_valve=1;
            show_infuse=1;
            show_withdrawal=1;
            show_output=1;
            do_ok=1;
        }
        else
        {
            if(command[1]=='e')
            {
                show_factors=1;
                do_ok=1;
            }
            if(command[1]=='p')
            {
                show_pos=1;
                do_ok=1;
            }
            if(command[1]=='r')
            {
                show_raw=1;
                do_ok=1;
            }
            if(command[1]=='f')
            {
                do_ok=1;
                show_calc=1;
            }
            if(command[1]=='v')
            {
                do_ok=1;
                show_valve=1;
            }
            if(command[1]=='i')
            {
                do_ok=1;
                show_infuse=1;
            } if(command[1]=='w')
            {
                do_ok=1;
                show_withdrawal=1;
            } if(command[1]=='o')
            {
                do_ok=1;
                show_output=1;
            }
        }

}
    Received command to cancel display of parameters to user...
        if(command[0]=='a')
        {
```

Figure 9F

```
            {
                if(command[1]=='e')
                {
                    show_factors=0;
                    do_ok=1;
                }
                if(command[1]=='p')
                {
                    show_pos=0;
                    do_ok=1;
                }
                if(command[1]=='r')
                {
                    show_raw=0;
                    do_ok=1;
                }
                if(command[1]=='f')
                {
                    show_calc=0;
                    do_ok=1;
                }
                if(command[1]=='v')
                {
                    do_ok=1;
                    show_valve=0;
                } if(command[1]=='i')
                {
                    do_ok=1;
                    show_infuse=0;
                } if(command[1]=='w')
                {
                    do_ok=1;
                    show_withdrawal=0;
                } if(command[1]=='o')
                {
                    do_ok=1;
                    show_output=0;
                }
            }
        }
Received command to continuously send/don't send parameters to user at regular
intervals...
    if(command[0]=='b')
    {
        if(command[1]=='0')
        {
            transmit=FALSE;
            do_ok=1;
        }
        if(command[1]=='1')
        {
```

Figure 7G

```
            transmit=TRUE;
            do_ok=1;
        }
    }

Received calibration command, calibration flags are set
    if(command[0]=='c')
    {
        if(command[1]=='a')
        if(command[2]=='1')
        {
            calibrating=TRUE;
            switch_valve(waste_1);
            clear_calibration_flags();
            do_ok=1;
        }
    }

Received command to echo sent characters back to the user (for cosmetic purposes)
    if(command[0]=='e')
    {
        if(command[1]=='0')
        {
            echo=FALSE;
            do_ok=1;
        }
        if(command[1]=='1')
        {
            echo=TRUE;
            do_ok=1;
        }
    }
Received command to change the motor run current
    if(command[0]=='g')
    {
            run_current=return_number(command,&err_in,1);

if(run_current>100)
            run_current=100;
            if(run_current<0)
            run_current=0;
            if(!err_in)
            {
                set_current(run_current);
                do_ok=1;
            }
    }
Received command to home the pump, resets homing flags
    if(command[0]=='h')
    {
        if(calibrating==FALSE)
        {
        do_home=TRUE;
        clear_homing_flags();
        set_position(0);
        delay_ms(50);
        set_position(0);
```

Figure 7H

```
            position=0;
            home_pin=FALSE;
            do_ok=1;
            }
        }
Received command to set automatic infusion rate
    if(command[0]=='i')
    {
        new_rate=(int32)return_number(command,&err_in,1);
        if(!err_in)
        {
            write_long_vars(addr_inf_rate,new_rate);
            write_vars(addr_inf_set,ADDRESSES_WRITTEN);
            read_long_vars(addr_inf_rate,&infusion_rate);
            do_ok=1;
        }
    }
Received command to change integral constant
    if(command[0]=='k')
    {
        ki=(float)return_number(command,&err_in,1);

if(ki>25)
        ki=(float)25;
        if(ki<1)
        ki=(float)1;

if(!err_in)
        {
            do_ok=1;
        }
    }
Received command to cycle dispense/fill continuously
    if(command[0]=='l')
    {
        if(command[1]=='o')
        if(command[2]=='o')
        if(command[3]=='p')
        {
            if(command[4]=='1')
            {
                do_loop=1;
                do_ok=1;

if(speed>0)
                am_i_filling=TRUE;
                else
                am_i_filling=FALSE;

}
        if(command[4]=='0')
            {
                do_loop=0;
                do_ok=1;
            }
        }
```

Figure 7I

```
    }
Received command to send back version number for firmware
    if(command[0]=='n')
    {
        sprintf(out_strings,"Scivex NanoFlow 1.4\r\n");
        com_host(out_strings);
    }
Received command to report piston position
    if(command[0]=='p')
    {
        sprintf(out_strings,"%ld\r\n",(int32)position);
        com_host(out_strings);
    }
Received command to report current speed
    if(command[0]=='r')
    {
        sprintf(out_strings,"%ld\r\n",(int32)speed);
        com_host(out_strings);
    }
Received command to set desired flow rate of pump if(command[0]=='s')
    {
        if(command[1]=='s')
            {
                waiting=TRUE;
                do_ok=1;
            }
        else
        {
            speed=return_number(command,&err_in,1);
            if(!err_in)
            {
                applied_speed=speed;
                do_ok=1;
                waiting=FALSE;
            }

}

// for(i=0;i<KD_LIMIT;i++)
        // derivative_array[i]=0.1;

}
Received command to change time constant for running average filter
    if(command[0]=='t')
    { i=(int)return_number(command,&err_in,1);

if(err_in==FALSE)
        {
        if(i<0)
        i=0;
        if(i>20)
```

write_vars(addr_time_const,i);
      read_vars(addr_time_const,&i);
      time_constant=i;
      do_ok=1;
      }
   }

Received command to immediately report parameters to user
   if(command[0]=='u')
   {
      report_values();

}
Received command to change the valve position
   if(command[0]=='v')
   {
      if(command[1]=='f')
      {
         switch_valve(fill);
         do_ok=1;
      } if(command[1]=='c')
      {
         switch_valve(column);
         do_ok=1;
      } if(command[1]=='1')
      {
         switch_valve(waste_1);
         do_ok=1;
      } if(command[1]=='2')
      {
         switch_valve(waste_2);
         do_ok=1;
      }

}
Received command to set automatic dispense rate
   if(command[0]=='w')
   {
      new_rate=(int32)return_number(command,&err_in,1);
      if(!err_in)
      {
         write_long_vars(addr_wit_rate,new_rate);
         write_vars(addr_wit_set,ADDRESSES_WRITTEN);
         read_long_vars(addr_wit_rate,&withdrawal_rate);
         do_ok=1;
      }
   }
Received command to set the first (zero flow) flow sensor response
   if(command[0]=='x')
```

Figure 7K

```
{
    i=(int16)return_number(command,&err_in,1);
    if(!err_in)
    {
        calibration_factor[0]=i;
```
Recalculate quadratic based on new number
```
get_abc(RATE_1,RATE_2,RATE_3,calibration_factor[0],calibration_factor[1],calibra
tion_factor[2]);
        write_vars(addr_1x,calibration_factor[0]);
        write_vars(addr_cal_set,ADDRESSES_WRITTEN);
        do_ok=1;
    }
}
```
Received command to set the second (moderate flow) flow sensor response
```
    if(command[0]=='y')
    {
        i=(int16)return_number(command,&err_in,1);
        if(!err_in)
        {
            calibration_factor[1]=i;
```
Recalculate quadratic based on new number
```
get_abc(RATE_1,RATE_2,RATE_3,calibration_factor[0],calibration_factor[1],calibra
tion_factor[2]);
        write_vars(addr_1y,calibration_factor[1]);
        write_vars(addr_cal_set,ADDRESSES_WRITTEN);
        do_ok=1;
        }
    }
```
Received command to set the third (high flow) flow sensor response
```
    if(command[0]=='z')
    {
        i=(int16)return_number(command,&err_in,1);
        if(!err_in)
        {
            calibration_factor[2]=i;
```
Recalculate quadratic based on new number
```
get_abc(RATE_1,RATE_2,RATE_3,calibration_factor[0],calibration_factor[1],calibra
tion_factor[2]);
        write_vars(addr_1z,calibration_factor[2]);
        write_vars(addr_cal_set,ADDRESSES_WRITTEN);
        do_ok=1;
        }
    }
```
Set current pump piston position
```
    if(command[0]=='@')
    {
        new_position=return_number(command,&err_in,1);
        if(!err_in)
        {
            set_position(new_position);
            do_ok=1;
        }
    } if(command[0]=='$')
        {
```

Figure 7L

```
            if(command[1]=='$')
            {
            cycle_timer=0;
            write_long_vars(addr_cyc_timer,0);
            do_ok=1;
            }
        }
```
Cancel calibration
```
    if(command[0]=='!')
    {
        calibrating=FALSE;
        clear_calibration_flags();

get_abc(RATE_1,RATE_2,RATE_3,calibration_factor[0],calibration_factor[1],calibration_factor[2]);
        do_ok=1;
    }
    if(do_ok)
    {
        sprintf(out_strings,"OK\r\n");
        com_host(out_strings);
        //clear_buffer(com_1_rec_buf,25);//added
    }
}//end source host
if(source==COM1)
{
    position=return_number(command,&err_in,0);//Get position information from
MicroLynx }
source=NONE;

}
```
Switches the valve position
```
void switch_valve(char a_position)
{
if(a_position==waste_1)
    {
        output_low(PIN_C3);
        output_high(PIN_C0);
        output_high(PIN_C1);
        output_high(PIN_C2);
        valve_position=1;
    } if(a_position==waste_2)
    {
        output_low(PIN_C2);
        output_high(PIN_C0);
        output_high(PIN_C1);
        output_high(PIN_C3);
        valve_position=4;
    } if(a_position==column)
    {
        output_low(PIN_C0);
```

Figure 7M

```
        output_high(PIN_C1);
        output_high(PIN_C2);
        output_high(PIN_C3);
        valve_position=3;
    } if(a_position==fill)
    {
        output_low(PIN_C1);
        output_high(PIN_C0);
        output_high(PIN_C2);
        output_high(PIN_C3);
        valve_position=2;
    }
}
```

Home the pump based on position of optical interrupt
```
void init(void)
{
int16 i=0;
char a_buffer[25];

clear_buffer(a_buffer,25);

if(!home_1&&!home_2)
    { switch_valve(waste_1);
        applied_speed=50000;

if(position>5000)
        {
           home_1=TRUE;
           set_position(150000);
           delay_ms(200);
           strcpy(a_buffer,"Finding home...\r\n");
           com_host(a_buffer);
           applied_speed=0;
           delay_ms(200);//added
           set_position(150000);//added
           delay_ms(200);//added

}

}
    else
    if(home_1&&!home_2)
    {
        switch_valve(fill);
        applied_speed=-100000;
        if(home_pin)
        {
           home_2=TRUE;
           strcpy(a_buffer,"home found...\r\n");
           com_host(a_buffer);
           applied_speed=5000;
```

Figure 7N

```
        do_home=FALSE;
        set_position(-2000);
        delay_ms(50);
        set_position(-2000);
        position=-2000;
        speed=0;
        applied_speed=0;
        do_home=FALSE;
        clear_homing_flags();
        home_pin=FALSE;
    }

}

}
```

The algorithm for finding the actual flow rate from raw sensor data in real time using the $ax^2+bx+c$ equation for a given solvent...

```
float return_actual_rate(int16 sensor_response)
{
//Roots of a quadratic...
float number=0;
float number2=0;

number=(float)sensor_response-(float)c_constant;

number2=(float)b_constant*(float)b_constant+((float)4*a_constant*(float)number)/
(float)1000;

if(number2>0)
    number2=(float)sqrt(number2);

number=((float)(-b_constant))+(float)number2;

number2=(float)((float)number/(float)((float)2*(float)a_constant))*(float)1000;

return number2;

}
```

The algorithm for finding the a, b, and c values of the quadratic from three data points collected at three different flow rates...

```
void get_abc(int16 f1, int16 f2, int16 f3,int16 r1, int16 r2, int16 r3)
{
//y=ax2 +bx +c, we want a,b,c
float number=0;
float number2=0;
char out_buf[25];

clear_buffer(out_buf,25);
```

Figure 70

```
    number=((float)r3/(float)f3)-((float)r1/(float)f3)+((float)r1/(float)f2)-
((float)r2/(float)f2);
    number2=((float)f3-(float)f2)/(float)1000;

a_constant=(float)number/(float)number2;
    b_constant=((float)r3/(float)f3)-(((float)a_constant*(float)f3)/(float)1000)-
((float)r1/(float)f3);
    c_constant=(float)r1;

}
```

The PID algorithm for pump speed control using negative feedback of actual flow sensor response...

```
float do_pid(float setpoint_speed,float measured_speed)
{
int i;

//The proportional signal
    the_proportional_error=(float)setpoint_speed-(float)measured_speed;

//The derivative average
    the_derivative_error=(float)(measured_speed-old_speed);
    old_speed=measured_speed;

if(the_derivative_error>250)
    the_derivative_error=(float)250;

derivative_array[derivative_index]=the_derivative_error;

derivative_index++;
    if(derivative_index>=KD_LIMIT)
    derivative_index=0;

the_derivative_error=0;
    for(i=0;i<KD_LIMIT;i++)
    the_derivative_error+=abs(derivative_array[i]);

the_derivative_error=the_derivative_error/(float)KD_LIMIT;

if(the_derivative_error==0)
    the_derivative_error=0.1;

the_integral_error=0;
    for(i=0;i<KD_LIMIT;i++)
    the_integral_error+=derivative_array[i];

//kd=(float)((float)250-the_derivative_error);
    kd=(float)(250)/(the_derivative_error);//was 350
    //kd=(float)((float)-0.12*the_derivative_error)+(float)40;

```
    kd=(float)40;
    if(kd<2)
    kd=(float)2;

speed_change=the_proportional_error*(float)kd;

return setpoint_speed+speed_change;

}
```

The calibration routine for determining flow sensor responses at three rates. Each of the rates are averaged for an entire turn of the pump lead screw.
```
int do_calibration(void)
{
int cal_is_done=FALSE;
char out_string[10]={'C','a','l','i',' ','D','o','n','e','\r'};
```

Set speed to 0
```
if(!cal_data_1&&!cal_data_2&&!cal_data_3)
    {
        applied_speed=RATE_1;
        cal_data_1=TRUE;
        delay_time=time+40;
    }
```
Get flow rate at no flow
```
if(cal_data_1&&!cal_data_2&&!cal_data_3)
    {
        if(time>=delay_time)
            {
                cal_data_2=TRUE;
                calibration_factor[0]=avg_flow_rate;

time_increment=0;
                delay_time=time+40;
                calibration_sum=0;
                applied_speed=RATE_2;

Set speed to moderate known level
```
if(cal_data_1&&cal_data_2&&!cal_data_3)
    {
        if(time>=delay_time)
            {
                calibration_sum+=(int32)avg_flow_rate;
                time_increment++;
```
Average flow rate for entire turn of lead screw...
```
                if(position>=required_volume)
                    {
                        cal_data_3=TRUE;
                        calibration_sum=calibration_sum/time_increment;
                        calibration_factor[1]=(int16)calibration_sum;

time_increment=0;
                        delay_time=time+40;
```

```
                        calibration_sum=0;
                        applied_speed=RATE_3;
                }
        }
        else
        required_volume=position+nl_per_turn;
    }
Set speed to known high level
if(cal_data_1&&cal_data_2&&cal_data_3)
    {
        if(time>=delay_time)
            {
                calibration_sum+=(int32)avg_flow_rate;
                time_increment++;
Average flow rate for entire turn of lead screw...
                if(position>=required_volume)
                    {
                        calibrating=FALSE;

calibration_sum=calibration_sum/time_increment;
                        calibration_factor[2]=(int16)calibration_sum;
                        applied_speed=0;
                        cal_is_done=TRUE;
                        write_vars(addr_1x,calibration_factor[0]);
                        write_vars(addr_1y,calibration_factor[1]);
                        write_vars(addr_1z,calibration_factor[2]);
                        write_vars(addr_cal_set,ADDRESSES_WRITTEN);

Calculate ax²+bx+c for the three flow sensor readings...
get_abc(RATE_1,RATE_2,RATE_3,calibration_factor[0],calibration_factor[1],calibra
tion_factor[2]);
                        com_host(out_string);
                }
        }
        else
        required_volume=position+nl_per_turn;
    } if(cal_is_done==TRUE)
return TRUE;
else
return FALSE;
}
Send system information to the user via RS-232
void report_values(void)
{
char out_strings[25];
int i;

clear_buffer(out_strings,25);

if(show_factors)
        { for(i=0;i<3;i++)
            {
                sprintf(out_strings,"%c=%ld\r\n",i+120,calibration_factor[i]);
```

Figure 7R

```
        com_host(out_strings);
        delay_ms(5);
    }

} if(show_pos)

sprintf(out_strings,"p=%ld\r\n",(signed int32)position);
    com_host(out_strings);
} if(show_valve)
{
    sprintf(out_strings,"v=%d\r\n",valve_position);
    com_host(out_strings);
} if(show_raw)
{
    sprintf(out_strings,"r=%ld\r\n",avg_flow_rate);
    com_host(out_strings);
} if(show_calc)
{
    sprintf(out_strings,"f=%ld\r\n",(signed int32)averaged_rate);
    com_host(out_strings);
} if(show_infuse)
{
    sprintf(out_strings,"i=%ld\r\n",infusion_rate);
    com_host(out_strings);
} if(show_withdrawal)
{
    sprintf(out_strings,"w=%ld\r\n",withdrawal_rate);//was float
    com_host(out_strings);
} if(show_output)
{
    sprintf(out_strings,"o=%ld\r\n",cycle_timer);//was float
    com_host(out_strings);
}
```

Figure 7S

FLOW SENSOR CALIBRATION METHODS AND APPARATUS

FIELD OF THE INVENTION

The invention relates to methods and apparatus for calibrating flow rate sensors used in liquid chromatography, mass spectrometry, and other analytical methodologies. More particularly, the invention relates to methods and apparatus useful for calibration of ultra-low flow rate liquid sensors used in micro/nano flow chromatography, mass spectrometry and other analytical applications.

BACKGROUND OF THE INVENTION

Analytical methods and systems have been developed that demand sensitive high-throughput analyses of biological materials in small quantities. Often, such analyses require precise control of the fluid flow rates in the range of about one (1) nano-liter (nL) per minute to about five (5) microliters (μL) per minute, with pressures varying over a range of several orders of magnitude. Such analytical applications include, among others, nano-scale liquid chromatography (nano-LC), mass spectrometry (MS), or capillary electrophoresis (CE). These microfluidic applications typically utilize fluid flow rates as low as tens of nanoliters per minute up to several microliters per minute. Designing systems to precisely achieve and maintain ultra-low flow rates is a difficult task, fraught with several potential problems.

One problem affecting such microfluidic techniques comes from the susceptibility of various components of systems used for conventional ultra-low flow applications to compress or decompress in response to a change in system pressure. This component adjustment to pressure change often creates a significant delay time before achieving a desired flow rate in conventional microfluidic systems and applications, and can also hinder accurate flow rate adjustment in such systems and applications.

Another persistent problem with such conventional microfluidic systems and applications occurs when air or other gases are inadvertently entrained into the flow path of such a system. If these compressible gases are present in the flow path of conventional systems for such applications, the compression and expansion of gas bubbles creates difficulties in achieving a desired flow rate.

In many conventional microfluidic systems, the flow rate of a fluid is established in a pump by displacing liquid at a controlled rate using, for example, a piston or syringe plunger. To obtain desired flow rates in such conventional systems, the displacing element of the pump is moved at a fixed velocity using a preprogrammed control system. Such conventional systems often show undesirable flow rate fluctuations created from imprecision in the mechanical construction of the drive system used to displace the liquid. In conventional lead screw-driven systems, for example, inaccuracies often arise from periodic changes in screw characteristics as the screw turns through a complete revolution, and from inaccuracies in thread pitch along the screw, among other types of mechanical errors.

In order to overcome these difficulties in achieving and maintaining desired flow rates, conventional flow sensors may be employed to allow the system to compensate for inaccuracies through use of a feedback loop to a preprogrammed control system.

Many conventional flow sensors used in microfluidic analysis, such as the SLG1430 sensor that is commercially available from Sensirion Inc. (of Zurich, Switzerland), have a non-linear response to fluid flow. For such flow sensors, the sensor response to increasing flow rate approximates a polynomial equation, with the equation order and constants dependent on variables such as flow sensor design, the liquid that is being monitored, and the operating flow rate range.

In order to use such conventional flow sensors to measure and maintain accurate ultra-low flow rates in conventional systems via a feedback loop, the sensor must be calibrated for the solvent that is to be passed through the sensor. Conventional calibration methods usually involve preparation of a list of the sensor responses at different flow rates for a given solvent. When a particular solvent is used, the actual flow rate is obtained by comparing the sensor response to tabulated calibration values gathered from repeated observations made for that particular sensor and solvent combination. Calibration curves for a given sensor and solvent can be obtained by fitting the calibration data to a best-fit curve from the empirical data in such conventional calibration methods.

A major problem with this conventional calibration tabular methodology is that data values must be collected for any solution mixture that is to be passed through the system. Doing so for numerous solvents can require a significant amount of time and effort. Moreover, for reliable operation, this data must be collected using a precise flow rate reference. Often, a conventional microfluidic system will be used to deliver different solutions that possess diverse characteristics, and calibrating a conventional system for these various solutions is often time consuming and laborious.

SUMMARY OF THE INVENTION

The present invention provides a method for calibrating a liquid flow sensor by pumping a volume of a fluid through the sensor for a series of fixed rates. The flow rate is first determined by moving a displacing element at a controlled velocity and, by use of a valve, allowing the system output to dispense through a low-pressure orifice or piece of tubing. Because the system is pumping at low pressure during the calibration procedure, system response is rapid, regardless of component compressibility or entrapped gas pockets. In fluidic systems that utilize lead screw drives, flow sensor response is determined by averaging the measured flow rate for a complete revolution of the pump lead screw, thereby minimizing periodic lead screw derived flow rate noise.

The flow sensor response is determined for several different flow rates, depending on the order of polynomial fit. In one embodiment, the sensor response is approximated using the general equation:

$$y = ax^2 + bx + c$$

where y is the sensor response, x is the actual flow rate, a is the first quadratic constant, b is the second quadratic constant, and c is the equation intercept, which is the sensor response measured with no fluid flow. In this embodiment, the constants can be determined by measuring the sensor response and actual flow rate at three individual pump infusion rates.

In another embodiment, during which a flow sensor can be calibrated during operation of an analytical system, the actual flow rate is determined by evaluating the quadratic equation using:

$$x = \frac{-b \pm \sqrt{b^2 - 4ac}}{2a}$$

using the real root. In this embodiment, x is determined from the measured flow sensor response.

In yet another embodiment, the sensor may be calibrated in the same general way over a larger flow rate range by extending the order of the polynomial and using more calibration data points to determine the constants.

It is an object of the invention to provide methods and apparatus which allow precise calibration of a flow sensor in a system which has periodic flow rate fluctuations.

It is another object of the invention to provide methods and apparatus which allow precise calibration of a flow sensor by minimizing the potential effects of trapped gases or compression of system components.

It is yet another object of the invention to provide methods and apparatus which allows precise calibration of a flow sensor for use with a given fluid over a wide range of flow rates.

It is yet another object of the invention to provide methods and apparatus to allow precise calibration of a flow sensor during operation of an analytical system to thereby allow an operator to obtain a desired flow rate.

It is an object of the invention to provide a method that accurately and precisely allows an operator to calibrate a flow sensor for a particular fluid more quickly and easily than conventional methods.

It is an object of the invention to provide a method which allows an operator to calibrate a flow sensor for a fluid without having to generate or use a table of empirical data.

It is an object of the invention to provide a method that allows precise flow control using inexpensive, mechanically-driven pump systems.

It is an object of the invention to provide a method that allows rapid in-situ calibration of a flow sensor while consuming small amounts of fluid.

These and other objects and advantages of the invention will be apparent from the following detailed description.

DETAILED DESCRIPTION OF THE DRAWINGS

FIGS. 7A–7S are examples of source code in accordance with the present invention.

DETAILED DESCRIPTION OF THE PREFERRED EMBODIMENT

Figure 1:
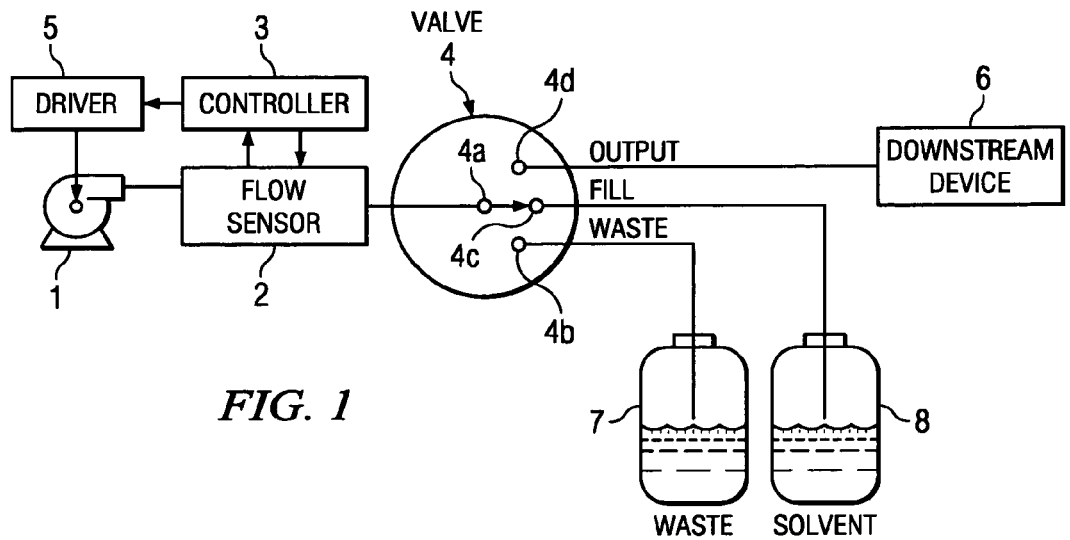
FIG. 1 is a schematic diagram of the components of a fluidic system in accordance with the present invention.

Referring to FIG. 1, the components of a fluid control system are depicted. It will be appreciated by those skilled in the art that the methods and apparatus of the invention may be used with chromatography, mass spectrometry, capillary electrophoresis, or other analytical applications and systems. As shown in FIG. 1, this particular embodiment of the fluid control system includes a selection valve 4 with a plurality of ports. One port 4a of valve 4 has a fluid connection to a first side of flow sensor 2. The second side of flow sensor 2 has a fluid connection to the input and output port of a pump 1. Those skilled in the art will appreciate that any one of a number of conventional selection valves, flow sensors, and pumps may be used for valve 4, sensor 2, and pump 1. For best results, I prefer to use the 100 μl positive displacement pump which is commercially available from Sapphire Engineering Inc. Pocasset, Mass., USA), the flow sensor SLG 1430 which is commercially available from Sensirion Inc. (Zurich, Switzerland), and the V-485 selection valve that is commercially available from Upchurch Scientific, Inc. (Oak Harbor, Wash., USA).

As shown in FIG. 1, the pump 1 is electronically connected to a controller 3 which, in turn, is electronically connected to a driver 5. The controller 3 is also electronically connected to the sensor 2. The controller 3 can be preprogrammed with computer software to perform the steps of the method of the invention. For best results, I prefer to use as the driver 5, a driver MICROLYNX® which is commercially available from Intelligent Motion Systems Inc. (of Marlborough, Conn., USA). The controller 3 preferably consists of a preprogrammed PIC 18F452 microcontroller, which is commercially available from Microchip Chandler, Ariz., USA) with serial communications and digital input/output connections. The controller 3 is essentially an application specific integrated circuit, with the computer program incorporated therein. The computer program preferably is written to allow the controller 3 and the system to perform the steps detailed below.

Still referring to FIG. 1, it can be seen that at least one of the output ports of valve 4 is in fluid communication with a waste receptacle 7. Another port of the valve 4 is in fluid communication with a reservoir 8, which holds the subject fluid to be considered for purposes of calibration (often referred to as the solvent). The port 4d of the valve 4 is in fluid connection with the input of a downstream analytical system 6. Those skilled in the art will appreciate that any of a number of analytical systems may represent the downstream analytical system, including chromatography or mass spectrometry systems.

The controller 3 is electronically connected to the valve 4, and controls the position of the valve 4. Those skilled in the art will appreciate that any of a number of analytical systems or devices may be attached to other unused ports on the chosen selection valve.

Figure 2:
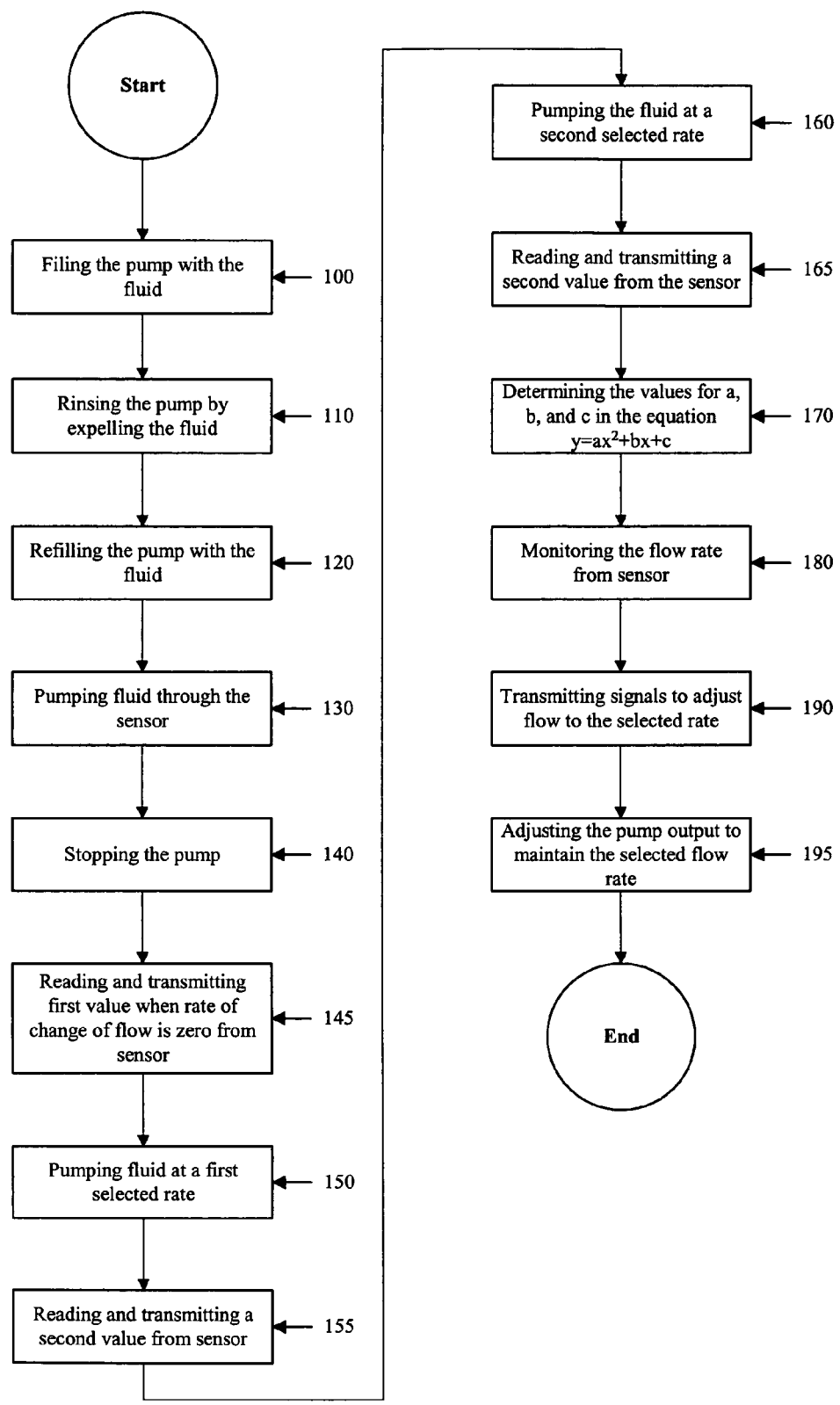
FIG. 2 is a flow diagram showing the steps of a method in accordance with the present invention.

Referring now to FIG. 2, the steps of the method of the invention will be described with respect to the flow diagram. (For ease of reference, the same numbers are used to refer to the components shown in FIG. 1.) Before beginning the calibration cycle, it is useful to first purge and prime the system to remove excess trapped air or other gases. Accordingly, step 100 is filling the pump 1 (in FIG. 1) from the reservoir 8 via the selection valve 4. Next, the pump 1 is rinsed 110 by expelling the fluid in the pump 1 to a waste receptacle via valve 4. The pump 1 is then refilled 120 with the fluid of interest. Together, steps 100, 110, and 120 can be considered the purging/priming cycle.

Still referring to FIG. 2, the calibration cycle is described next. In step 130, an operator pumps a volume of the fluid through the sensor 2 to a waste receptacle via the valve 4. There will be negligible pressure present in the system during this step 130. The operator then stops the pump 1 and the flow of the fluid through the sensor 2 at step 140. Once the rate of change of flow sensed by the sensor 2 has minimized, the flow sensor will output this value and transmit it to the controller 3 as step 145. This value transmitted to the controller 3 at step 145 will be considered the constant c in the equation $y=ax^2+bx+c$ in the quadratic equation (or, if the controller is programmed to solve a cubic or other equation, the value shall be deemed the constant in such equation corresponding to the y-intercept in the equation).

During the next step 150, the operator then starts the pump 1 to pump the fluid so that it flows at a preselected rate, such as 2 microliters per minute through the sensor 2 and to a waste receptacle. The rate of flow can be determined by knowing the linear distance that the piston of the pump 1 travels based on the pitch of the lead screw thread that drives the piston of the pump 1. The cross-sectional area of the piston in pump 1 is also known. Thus, the volume of the fluid moved per unit time per rotation of the lead screw (or the lead screw nut, as the case may be) is known or readily determined. For best results, the calibration step 150 should be performed only with the output of the fluid flowing to waste so that there is negligible back pressure within the microfluidic system and therefore any elasticity of any components within the system will not be of significance in the calibration. Once the preselected first flow rate is reached, the sensor 2 will transmit a second averaged value to the controller 3 at step 155. This averaged value is determined by averaging the flow sensor response for the entire cycle of periodic noise in the pump mechanism. In the case of a lead screw driven pump, the flow rate is averaged for a complete turn of the lead screw.

Still referring to FIG. 2, the operator then sets the pump 1 to pump the fluid so that it flows at a second preselected rate at step 160, such as 4 microliters per minute, through the sensor 2 and to a waste receptacle. As noted above, the rate of flow can be determined precisely by knowing the dimensions of the distance traveled by the lead screw of the piston of pump 1 and the area of the piston in pump 1. In step 165, once the second preselected flow rate is reached, the sensor 2 will transmit a third value to the controller 3. This averaged value is determined by averaging the flow sensor response for the entire cycle of periodic noise in the pump mechanism. In the case of a lead screw driven pump, the flow rate is averaged for a complete turn of the lead screw.

For the highest order n in the equation to be solved, we prefer to measure and determine the sensor 2 responses for n+1 different flow rates. By using the measured flow sensor 2 responses and the known pumping rate of the fluid for the corresponding sensor 2 output responses, the operator can determine at step 170 the constants a, b, and c for the quadratic equation (and other constants where the equation to be used has higher orders than the second). Alternatively, the controller 3 can be preprogrammed to determine 170 the values of the constants.

Once the sensor 2 has been calibrated in accordance with the invention, the system can be used by the operator as follows: The operator can for example read the output of the flow sensor 2 during operation of the system at step 180. The flow rate value output by the sensor 2 can also be determined automatically by the preprogrammed controller 3. The controller 3 can be preprogrammed so that it transmits appropriate signals to driver 5 at step 190 depending on the incremental values of flow rate of change measured by the sensor 2 and transmitted to the controller 3. The driver 5 then adjusts the output of the pump 1 based on the signals received by sensor 2 to maintain the flow rate set by the operator of the system at step 195.

Although not shown (apart from controller 3), those skilled in the art will appreciate that a preprogrammed computer can be used as the controller 3. Those skilled in the art will appreciate that such a computer can be easily programmed to receive and store the values it receives from the sensor 2, together with the information for determining the flow rate based on the dimensions of the pump. The programmed computer can be set so that it automatically calculates the constants a, b, and c (or others depending on the particular equation to be solved) and then outputs those values for use by the operator. Similarly, the computer (not shown apart from controller 3) can be preprogrammed with such constants so that the computer receives updated signals corresponding to the flow rate as determined by the sensor 2 during operation, the computer (not shown apart from controller 3) and, as appropriate according to its programmed instructions, sends signals to the driver 5 to adjust the pump 1 to obtain the flow rate selected by the operator for operation of the system 1. Those skilled in the art will appreciate that such computer programs can be stored on the hard drive of the computer (not shown apart from controller 3), or on a disk, CDROM, DVD, EEPROM, ASIC, per drive, or other electronic storage device with non-volatile memory.

Figure 3:
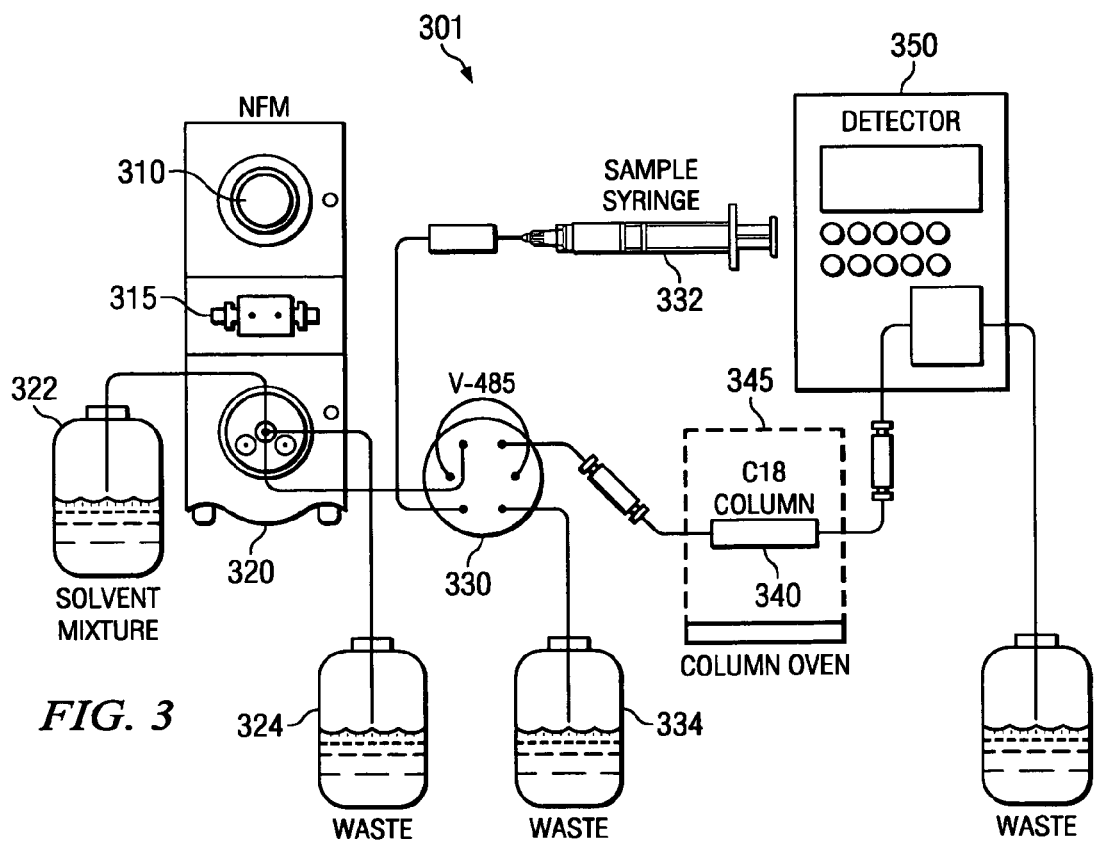
FIG. 3 is a schematic diagram of a system used to provide an example test of the methods of the present invention.

Referring now to FIG. 3, an experimental system 301 used to evaluate one embodiment of the invention is shown. In FIG. 3, the system 301 includes a high-pressure positive displacement pump 310, an inline non-invasive flow sensor 315, and a four-way selection valve 320 (for filling and dispensing solvent mixtures in the system 301). The system 301 maintains a precise flow rate to a desired value regardless of back pressure in system 301. The system 301 is able to use the output signal from the flow sensor 315 to adjust the piston velocity of the pump 310 to clamp the output flow rate from the pump 310 to the selected value. As shown in FIG. 3, the experimental system 301 also includes a source of a solvent 322, which is in fluid communication with the flow sensor 315. The flow sensor 315, in turn, is connected to allow fluid communication with both a waste receptacle 324 and an injection valve 330. The injection valve is also in fluid communication with a sample syringe 332 and a second waste receptacle 334. In addition, the injection valve 330 is in fluid communication with a first end of a column 340, which is housed within a column oven 345. The column oven 345 is used to maintain the temperature of the column 340 at 35.0° C.±0.05° C. The second end of the column 340 is in fluid communication with a detector 350. For this experiment, I used a V-485 NANOPEAK injection valve (commercially available from Upchurch Scientific of Oak Harbor, Wash.) for the injection valve 330, a 15 cm by 75 μm inner diameter nano column (the PEPMAP C18 column commercially available from LC Packings of Amsterdam, The Netherlands) for the column 340, and an ULTIMATE UV detector (also commercially available from LC Packings of Amsterdam, The Netherlands) for the detector 350.

Figure 4:
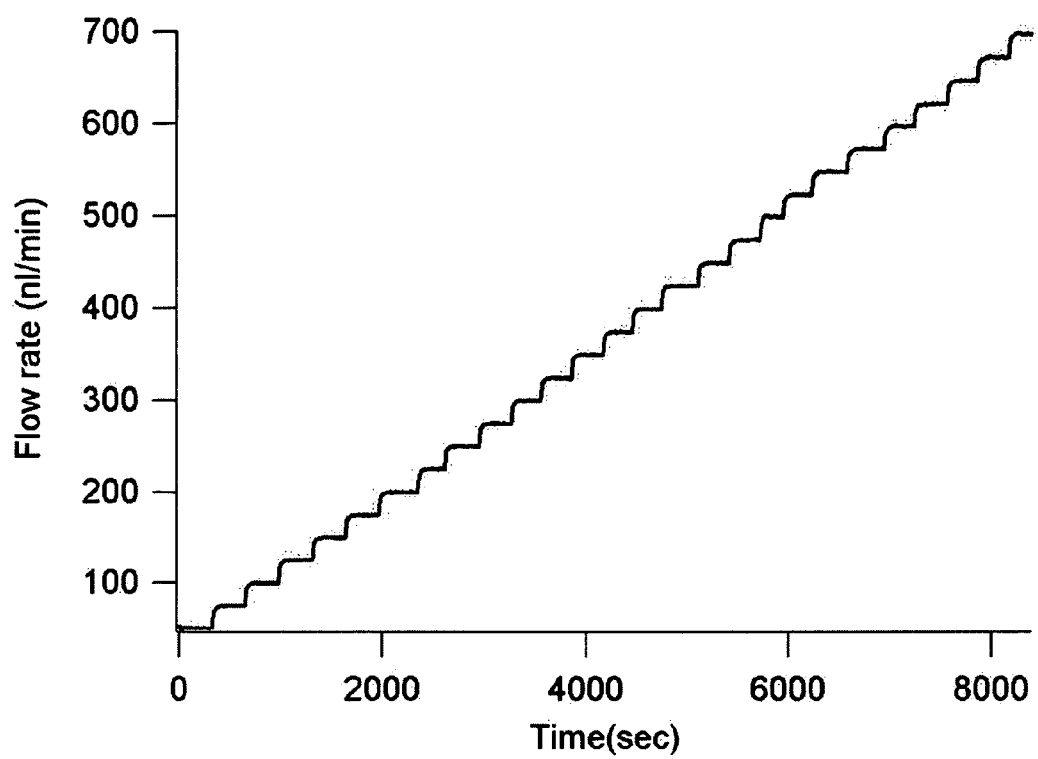
FIG. 4 is a graph showing the data collected in one example of the present invention.

Using a timed injection routine, numerous 5 nL plugs of a mixture consisting of naphthalene, fluorine, biphenyl, and uracil dissolved in 75% acetonitrile/water were repeatedly injected into the column 340. Analytes were detected via absorbance at 250 nm using the detector 350. All experimental data were collected at 1.6 Hz using analog/digital circuitry and preprogrammed computer software performing the methods described above. The data collected are shown graphically in FIG. 4. As shown in FIG. 4, the system flow sensor output for a variety of increasing flow rates applied to the column 340 (over a range of 50 nL/minute to 700 nL/minute) shows that the system flow sensor possesses a 90% risetime of 12 seconds at 700 nL/minute (a pressure of 3,000 psi) and exhibits a RMS flow rate noise of approximately 1 nL/minute at an output flow rate of 50 nL/minute.

Figure 5:
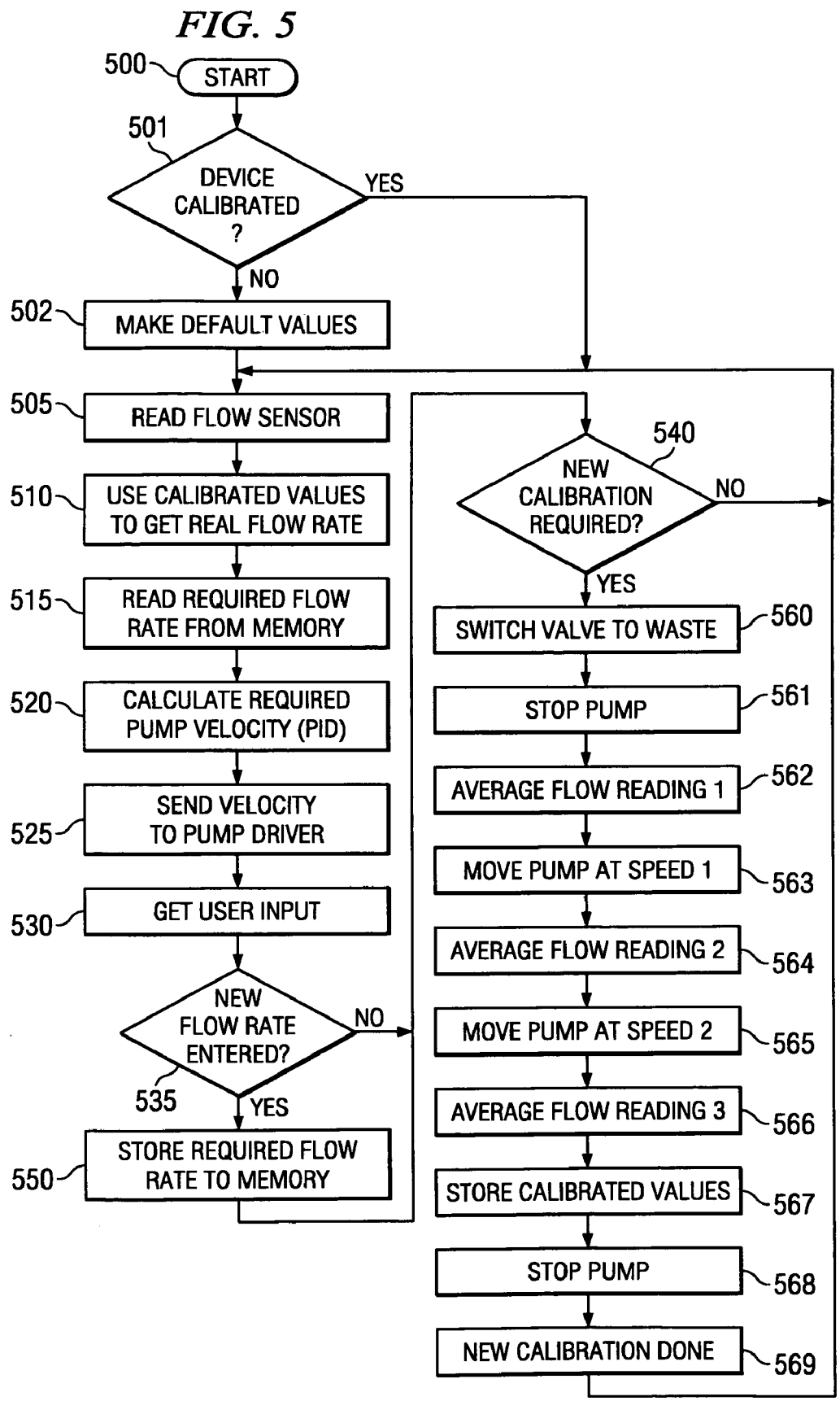
FIG. 5 is a flow diagram showing an alternative embodiment of the present invention.

Referring now to FIG. 5, a flow chart of an another alternative embodiment of the present invention is shown. In step 500, the system begins the methods of the invention. In step 501, the system checks to see if the flow sensor has already been calibrated. This can be done by checking a flag or the status of a value stored in computer memory. If the flow sensor has been determined to have been calibrated at step 501, then the next step is reading the data value from the flow sensor at step 505. This step 505 is repeated as many times as is necessary to obtain the data values needed to calculate the constants for the polynomial equation to be solved. If the equation is of the order n, then at least n+1 data values should be measured. For example, if the flow sensor is known to have a non-linear response that is quadratic, then the program will need to measure at least three data values in order to solve the equation $y=ax^2+bx+c$. Similarly, if the equation used to model the response of the flow sensor is cubic, then at least four data values should be read from the flow sensor.

Still referring to FIG. 5, the data values read in step 505 are provided to the preprogrammed computer (not shown in FIG. 5) so that it can use the data values measured by the flow sensor to calculate the constants and solve the polynomial equation. By solving the equation, the computer has calculated a value for the real flow rate of the system at step 510. Next, at step 515, the computer reads the required flow rate from memory. This value can be input by the operator when setting up the system. At step 520, the computer then calculates the required pump velocity needed to achieve the preselected flow rate based on the value of the real flow rate and the stored value for the desired flow rate. At step 525, the computer then sends a signal to the pump driver in order to have the pump operate at the required velocity determined in step 520. At step 530, the system checks to see if the user or operator has input a new flow rate. If not, the next step is to determine if a new calibration is required. Of course, an operator may choose to calibrate based on the passage of time of after some other selected interval or event has occurred. If not, the next step is to repeat step 505 and continue the foregoing cycle. If a user has input a new flow rate, the system first stores the new value in computer memory at step 550, as shown in FIG. 5. The system then checks to see whether a new calibration is required at step 540.

Still referring to FIG. 5, if the computer determines that a new calibration is needed at step 540, the computer then performs the following steps. First, the computer sends a signal to the valve (not shown in FIG. 5) to switch the fluid communication with at least one valve port to a waste receptacle at step 560. Next, at step 561, the computer sends a signal to stop the pump. At step 562, the data value is read from the flow sensor. Although this can be a single data reading, I prefer to have a number of readings taken on the flow sensor's reading, each of which can be stored in the computer memory and then averaged. Once the average has been obtained in step 562, the computer sends a signal to have the pump operate at a preselected first speed at step 563. In step 564, a number of values are read from the flow sensor, stored in computer memory and an average of those values is determined. Next, in step 565, the computer sends a signal to the pump to have it operated at a second preselected speed. In step 566, a number of readings are taken of the flow sensor, stored in computer memory, and an average is determined. In step 567, the computer stores the values for the averages determined in the steps 562, 564, and 566 in computer memory. At step 568, the computer then sends a signal to stop the pump. The computer then calculates the constants for the polynomial equation corresponding to the flow sensor using a least-squares algorithm (sometimes referred to as a "best square fit"), or a similar algorithm. Once the constants have been calculated and the equation solved, the computer can use those values in the equation based on the new required flow rate input and the new calibration is completed at step 569. Once the new calibration is completed at step 569, the computer can then repeat the performance of the steps by returning to step 505 and reading the values of the flow rate from the flow sensor.

Figure 6:
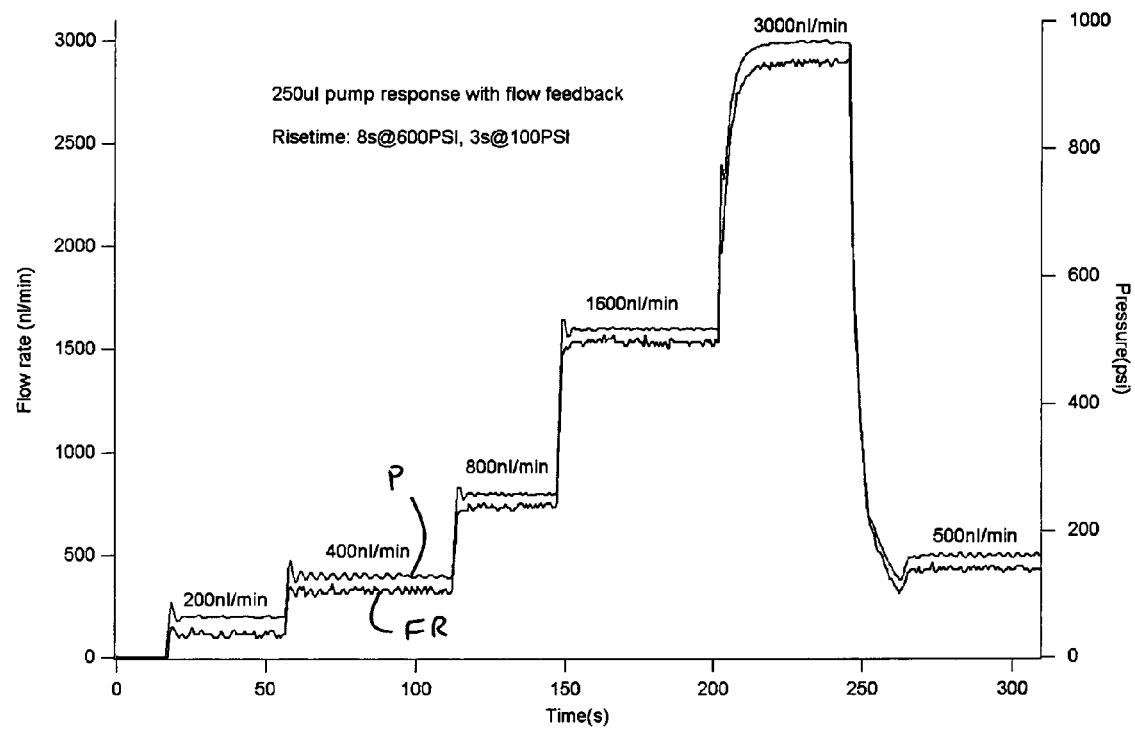
FIG. 6 is a graph showing data collected in another example of the present invention.

Referring now to FIG. 6, data from another example of the present invention is provided in graphical form. In FIG. 6, the flow rate FR is shown, as is the measured pressure P. FIG. 6 shows that the pressure P rapidly adjusts to changes made to the flow rate in a system using the methods of the present invention.

Now referring to FIGS. 7A–7S, source code of a computer program is provided, in accordance with one embodiment of the present invention. The source code shown in FIGS. 7A–7S may be used to implement some or all of the steps of the methods of the present invention as described above.

Those skilled in the art will appreciate that the methods of the invention can be used to attenuate noise from mechanical sources, such as the leadscrew of the pump. This can be done by averaging the values obtained from the flow sensor over one entire rotation of the leadscrew. For example, when a stepping motor (not shown) is used to actuate the pump, the number of steps corresponding to a complete rotation of the leadscrew can be determined. For example, in the system used in the above example, the stepping motor (not shown) has 200 steps per complete revolution, and a complete revolution of the leadscrew pumps 5 µL of the fluid. At a rate of 1.56 Hz, the computer is able to obtain 94 data points per minute, all of which can be stored in memory of the computer and then averaged. This averaging eliminates the variations which can result from the mechanical variations in the leadscrew due to thread size and the like. Those skilled in the art will appreciate that this method can also be used to calibrate any mechanical pump that provides periodic noise (i.e., fluctuations in the data due to various mechanical features) by averaging the data values obtained over the entire period of the noise source, thus allowing a user to calibrate for noise from such pumps with drive mechanisms other than leadscrews.

Attached hereto as Appendix A, and incorporated fully by reference herein, is a copy of the User Guide—100 µL version for the Scivex Confluent Nano Fluidic Module. This Appendix A provides further details and information regarding the use of calibration methods and apparatus of the present invention, such as in the operation of a pump controlled by a preprogrammed computer which uses values measured by a flow sensor to calculate a solution to a polynomial equation, such as is described above, then uses the calculated values to determine what, if any, adjustments to the pump's actions need to be made to obtain a preselected flow rate.

Those skilled in the art will appreciate that the data points obtained using the methods of the invention can be used to perform other interpolation algorithms, such as a cubic spline. Such techniques include those described in the book "Numerical Recipes in C: The Art of Scientific Computing" by William H. Press, published by the Cambridge University Press in 1988, which is hereby incorporated by reference herein. Those of skill in the art will also appreciate that the methods of the invention can be used with other equipment and solution combinations. For example, a system using two pumps (not shown) and two solutions (not shown) that are mixed together using a T-junction (also not shown) can be used for a binary gradient system.

The foregoing description of the invention is of the preferred embodiments and should not be considered a limitation on the scope of the invention claimed. Those skilled in the art will appreciate that changes may be made in the use of specific components, solutions, sample sizes, flow rates, and the like without departing from the spirit of the invention and the scope of the claims.

I claim:

1. An article of manufacture comprising: an electronic storage device comprising computer software having program instructions directing a computer running said instructions to receive and store in memory a first value for a first flow rate from a microfluidic fluid flow sensor, receive and store in memory a second value for a second flow rate from said flow sensor, receive and store in memory a third value for a third flow rate from said flow sensor, calculate values for constants a, b, and c corresponding to said first, second and third values for calibration of said flow sensor, receive and store in memory an operational value for a flow rate from said flow sensor during operation, calculate a real flow rate corresponding to the operational flow rate value, and adjust a pump velocity based on the calculated real flow rate.

2. The article according to claim 1 wherein said article comprises a hard disk.

3. The article according to claim 1 wherein said article comprises a CDROM.

4. The article according to claim 1 wherein said article comprises a non-volatile computer memory device.

5. The article according to claim 1 wherein said program instructions further direct the computer to adjust the flow rate of a pump responsive to the flow rate calculated using the values calculated for constants a, b, and c.

6. A method of controlling flow rate in a microfluidic liquid chromatography system comprising a pump in fluid communication with a flow sensor comprising the steps of:
   pumping a fluid in the system at (n+1) preselected flow rates, and determining the corresponding value for each rate of flow from the flow sensor;
   calculating n constants for a polynomial equation with n as the highest order;
   measuring a flow rate from the flow sensor;
   calculating a real flow rate corresponding to the measured flow rate using the polynomial equation; and
   adjusting the pump velocity based on the calculated real flow rate.

7. The method according to claim 6 wherein n equals 3.

8. The method according to claim 6 wherein the values of the n constants are calculated using the equation $y=ax^2+bx+c$.

9. The method according to claim 6 wherein the values of the n constants are calculated using a least-squares algorithm.

10. The method according to claim 6 wherein the flow sensor comprises a thermal anemomity sensor.

11. The method according to claim 6 wherein the fluid comprises one selected from a group consisting of the following: tetrahydrofuran, methanol, water, ethanol, dimethylsulfoxide, and acetonitrile.

12. The method according to claim 6 further comprising the steps of first rinsing a pump used for pumping the fluid.

13. The method according to claim 6 wherein the steps of pumping the fluid through the flow sensor further comprises pumping the fluid through a valve to a waste receptacle.

14. The method according to claim 6 further comprising the step of providing a pump with a known flow rate.

15. The method according to claim 6 further comprising the steps of transmitting the first, second, and third values from the sensor to a computer.

16. The method according to claim 6 wherein the calculating step is performed by a computer in accordance with a computer program.

17. The method according to claim 6 wherein the first flow rate is between approximately −1000 microliters per minute or so and approximately +1000 microliters per minute or so.

18. The method according to claim 6 wherein the second flow rate is between about −5000 microliters per minute or so and about +5000 microliters per minute or so.

19. The method according to claim 6 wherein n equals four.

20. The method according to claim 19 wherein the values of the n constants are calculated using the equation $y=ax^3+bx^2+cx+d$.

* * * * *